(12) United States Patent
Yoshida et al.

(10) Patent No.: US 7,432,228 B2
(45) Date of Patent: Oct. 7, 2008

(54) INHIBITOR AGAINST BIOSYNTHESIS OF ABSCISIC ACID

(75) Inventors: Shigeo Yoshida, Tokyo (JP); Tadao Asami, Tokyo (JP)

(73) Assignee: Riken, Saitama (JP)

( * ) Notice: Subject to any disclaimer, the term of this patent is extended or adjusted under 35 U.S.C. 154(b) by 234 days.

(21) Appl. No.: 11/362,415

(22) Filed: Feb. 27, 2006

(65) Prior Publication Data

US 2006/0148650 A1 Jul. 6, 2006

Related U.S. Application Data

(62) Division of application No. 10/490,214, filed as application No. PCT/JP02/10364 on Oct. 4, 2002, now Pat. No. 7,098,365.

(30) Foreign Application Priority Data

Oct. 5, 2001 (JP) .............................. 2001-309508

(51) Int. Cl.
 *A01N 47/06* (2006.01)
(52) U.S. Cl. ..................................... 504/306
(58) Field of Classification Search .................. None
 See application file for complete search history.

(56) References Cited

U.S. PATENT DOCUMENTS

| | | | |
|---|---|---|---|
| 4,282,551 | A | 8/1981 | Berney |
| 4,353,734 | A | 10/1982 | Seres et al. |
| 4,874,420 | A | 10/1989 | Wroblowsky et al. |
| 4,960,939 | A | 10/1990 | Eloranta |
| 5,399,564 | A | 3/1995 | Hackler et al. |
| 5,597,836 | A | 1/1997 | Hackler et al. |
| 5,922,648 | A | 7/1999 | Lorenz et al. |

FOREIGN PATENT DOCUMENTS

| | | |
|---|---|---|
| EP | 0385952 | 9/1990 |
| JP | 52-131564 | 11/1977 |
| JP | 61-122251 | 6/1986 |
| JP | 6-501715 | 2/1994 |
| JP | 06293730 A2 | 10/1994 |
| JP | 10251234 | 9/1998 |
| WO | 93/05050 | 3/1993 |
| WO | 97/11078 | 3/1997 |

OTHER PUBLICATIONS

R. Creelman et al., Plant Physiology, vol. 99, 1992, pp. 1258-1260.
S. Iuchi et al., The Plant Journal, vol. 27, No. 4, 2001, pp. 325-333.
English Language Abstract of JP 10-251234.
H. Heaney et al., Tetrahedron, vol. 51, 1995, pp. 10737-10750.
Kita, Yasuyuki et al: "An Oxidative Intramolecular Phenolic Coupling Rection for the Synthesis of Amaryllidaceae Alkaloids Using a Hypervalent Iodine (III) Reagent", Journal of Organic Chemistry,61(17), 5857-5864 CODEN: JOCEAH; ISSN: 0022-3263, 1996, XP002345208.
Buck, Johannes S.: "Some substituted di( .beta.-phenylethy1)amines and benzyl-.beta.-phenylethylamines", Journal of the American Chemical Society, 53, 2192-200 CODEN: JACSAT; ISSN: 0002-7863, 1931,XP002345209.
Di Plama, Joseph R. et al.: "Relation of chemical structure to antifibrillatory potency of certain .alpha.-fagarine-like compounds", Journal of Pharmacology and Experimental Therapeutics, vol. 98, 1950, pp. 251-257, XP008052543; Rockville Pike, US.
Chem. Abstracts 1995:578508; abstract of JP 06293730, published Oct. 21, 1994.
Surrey et al. ("Antifibrillatory Agents. The Preparation of Some N-Benzyl-N-methylphenethylamines", Journal of the American Chemical Society (1949), 71, 2421-2.).
Y. Xia et al., "Substituted 1,3,5-Triazines as Cholesteryl Ester Transfer Protein Inhibitors", Bioorganic and Medicinal Chemistry Letters, vol. 6, No. 7, pp. 919-922 (1996).
English Language translation of Japanese Office Action Issued in JP 2001-309508, dated Jan. 30, 2007.

*Primary Examiner*—Samuel A Barts
(74) *Attorney, Agent, or Firm*—Greenblum & Bernstein, P.L.C.

(57) ABSTRACT

Compounds represented by the following general formula (I) or salts thereof:

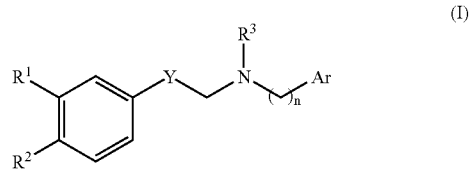

(I)

wherein $R^1$ represents hydrogen atom, hydroxyl group, or an alkoxy group; $R^2$ represents hydroxyl group or an alkoxy group which may be substituted; $R^3$ represents hydrogen atom or an alkyl group which may be substituted; Y represents —CH=CH— or —CH$_2$—; n represents 0 or 1; Ar represents an aryl group which may be substituted or a heteroaryl group which may be substituted, which are useful as inhibitors against the abscisic acid biosynthesis and plant growth regulators.

12 Claims, No Drawings

INHIBITOR AGAINST BIOSYNTHESIS OF ABSCISIC ACID

CROSS-REFERENCE TO RELATED APPLICATIONS

This application is a divisional of application Ser. No. 10/490,214, filed Oct. 4, 2002, now U.S. Pat. No. 7,098,365 which is a National Stage Application of International Application No. PCT/JP02/10364, filed Oct. 4, 2002, which was not published in English under PCT Article 21(2), entering the National Stage on Mar. 31, 2004, and which claims priority of Japanese Application No. 2001-309508, filed Oct. 5, 2001. The entire disclosure of application Ser. No. 10/490,214 is considered as being part of this application, and the entire disclosure of application Ser. No. 10/490,214 is expressly incorporated by reference herein in its entirety.

TECHNICAL FIELD

The present invention relates to a compound having inhibitory action against abscisic acid biosynthesis or a salt thereof, and also to an inhibitor against the abscisic acid biosynthesis or a plant growth regulator comprising said compound or a salt thereof as an active ingredient.

BACKGROUND ART

Abscisic acid is a plant hormone that involves in plant responses to various environmental stresses. For example, when a plant is suffered from dry stress, abscisic acid is rapidly accumulated, and then, pore closing and expression of stress-related genes such as rab18, kin1, and rd29B are promoted. As for abscisic acid biosynthesis in plants, a major pathway involves, via a carotenoid of a compound comprising 40 carbon atoms, use of xanthoxin having 15 carbon atoms as a precursor, which is generated by the degradation of the carotenoid, and oxidation of the hydroxyl group at the 3'-position, the isomerization of the double bond derived from the epoxy cleavage; and the oxidation of the aldehyde into carboxylic acid. In particular, the cleavage reaction of epoxycarotenoid by dioxygenase [nine-cis-epoxycarotenoid dioxygenase (NCED)] into xanthoxin is considered as a reaction that controls the abscisic acid biosynthesis.

In order to elucidate physiological functions of abscisic acid, which is a plant hormone essential for plant growth, methods has been used so far wherein abscisic acid is directly applied to a plant, or wherein a mutant whose gene for the abscisic acid biosynthesis is destroyed is used to analyze expressed physiological phenomena. However, by the application of abscisic acid, which already exists in the plant body, it is difficult to elucidate actual physiological actions of inherent abscisic acid. The methods using the mutants, which are in deficient stage of abscisic acid, are useful for investigation of the functions of abscisic acid by comparison with wild strains in physiological phenomena and morphologic states. However, the methods have disadvantages in that they are inapplicable to various plants and the abscisic acid deficient state cannot be controlled in a desired growth period.

As a method for compensating the disadvantages of the methods available to date, inhibitors against the abscisic acid biosynthesis can be utilized. In order to artificially obtain an abscisic acid deficient plant, agents inhibiting the biosynthesis of carotenoid, which is an intermediate of the abscisic acid biosynthesis, have already been used; however, such agents have potent whitening action, and accordingly, they are inappropriate for investigation of an abscisic acid deficient state without involvement of side effects. Under these circumstances, if a specific inhibitor against abscisic acid can be provided, various plants can easily be introduced in an abscisic acid deficient state, and analytical studies of abscisic acid functions can be expectedly progressed. In addition, an abscisic acid biosynthesis inhibitor can be utilized as a plant growth regulator which is effective for various growth processes of plants. It has been reported that NDGA [4,4'-(2,3-dimethyl-1,4-butanediyl)bis-1,2-benzenediol] which is known as a peroxidase inhibitor has inhibitory action on the abscisic acid biosynthesis on the basis of the results of inhibitory test of pore closing activity and the analysis of the amount of inherent abscisic acid production (Plant Physiology (1992) 99, 1258-1260).

DISCLOSURE OF THE INVENTION

An object of the present invention is to provide a compound having inhibitory action against the abscisic acid biosynthesis. The inventors of the present invention conducted intensive studies to achieve the foregoing object. As a result, they found that the compounds represented by the following general formula (I) or salts thereof have inhibitory action against the abscisic acid biosynthesis, and that they were useful as plant growth regulators. The present invention was achieved on the basis of these findings.

The present invention thus provides a compound represented by the following general formula (I):

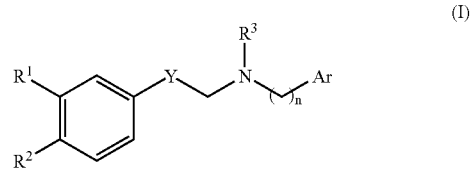

(wherein $R^1$ represents hydrogen atom, hydroxyl group, or an alkoxy group; $R^2$ represents hydroxyl group or an alkoxy group which may be substituted; $R^3$ represents hydrogen atom or an alkyl group which may be substituted; Y represents —CH=CH— or —CH$_2$—; n represents 0 or 1; Ar represents an aryl group which may be substituted or a heteroaryl group which may be substituted) or a salt thereof.

From another aspect of the present invention, there are provided an inhibitor against the abscisic acid biosynthesis which comprises the compound represented by the aforementioned general formula (I) or a salt thereof as an active ingredient; an epoxycarotenoid dioxygenase inhibitor which comprises the compound represented by the aforementioned general formula (I) or a salt thereof as an active ingredient; a plant growth regulator which comprises the compound represented by the aforementioned general formula (I) or a salt thereof as an active ingredient; and a use of the compound represented by the aforementioned general formula (I) or a salt thereof for the manufacture of the aforementioned inhibitor or the aforementioned regulator.

The present invention further provides a method for inhibiting the abscisic acid biosynthesis in a plant body, which comprises the step of applying the compound represented by the aforementioned general formula (I) or a salt thereof to a plant; a method for inhibiting epoxycarotenoid dioxygenase in a plant body, which comprises the step of applying the compound represented by the aforementioned general formula (I) or a salt thereof to a plant; and a method for regulating plant growth, which comprises the step of applying the compound represented by the aforementioned general formula (I) or a salt thereof to a plant.

BEST MODE FOR CARRYING OUT THE INVENTION

As the alkoxy group represented by $R^1$, for example, a linear or branched alkoxy group having 1 to about 6 carbon atoms can be used. Preferably, an alkoxy group such as methoxy group, ethoxy group and n-propoxy group can be used, and more preferably, methoxy group can be used. As $R^1$, hydrogen atom or methoxy group is preferred. As the alkoxy group represented by $R^2$, which has the same definition as the above, methoxy group can preferably be used. When the alkoxy group represented by $R^2$ is substituted, types, numbers, and substituting positions of substituents are not particularly limited. For example, substituents containing oxygen atom such as an alkoxycarbonyl group, carboxyl group and hydroxyl group are preferred. As the substituted alkoxy group represented by $R^2$, for example, an alkoxycarbonyl-substituted alkoxy group is preferred, and more preferably, methoxycarbonyl-substituted methoxy group can be used. As $R^2$, hydroxyl group, methoxy group, or methoxycarbonyl-methoxy group is preferred.

The alkyl group represented by $R^3$, for example, a linear or branched alkyl group having 1 to about 6 carbon atoms can be used. Preferably, an alkyl group such as methyl group, ethyl group and n-propyl group can be used, and more preferably, methyl group can be used. When the alkyl group represented by $R^3$ is substituted, types, numbers, and substituting positions of substituents are not particularly limited. For example, substituents containing oxygen atom such as an alkoxycarbonyl group, carboxyl group and hydroxyl group are preferred. As $R^3$, hydrogen atom, methyl group, or methoxycarbonylmethyl group is preferred.

Examples of the aryl group represented by Ar include phenyl group, naphthyl group and the like, and preferably, phenyl group can be used. As the heteroaryl group represented by Ar, for example, a 5-10 membered heteroaryl group which contains one or more heteroatoms selected from the group consisting of nitrogen atom, oxygen atom, and sulfur atom as the ring constituting atoms can be used. More preferably, a 5- or 6-membered heteroaryl group which contains one or two nitrogen atoms or oxygen atoms as the ring constituting atoms can be used, and further preferably, a 5- or 6-membered heteroaryl group which contains one nitrogen atom or oxygen atom as the ring constituting atom can be used. More specifically, pyridyl group, furyl group or the like is preferred as the heteroaryl group. When the aryl group or the heteroaryl group represented by Ar is substituted, types, numbers, and substituting positions of substituents are not particularly limited. For example, the aryl group or the heteroaryl group is preferably substituted with 1 or about 2 substituents such as hydroxyl groups, alkoxy groups (for example, methoxy group), halogen atoms (for example, fluorine atom, chlorine atom and bromine atom). Preferred substituents include hydroxyl group, methoxy group, and fluorine atom. When Ar is phenyl group, the phenyl group is preferably substituted at the 3- and/or 4-position.

The compounds represented by the general formula (I) may sometimes have one or more asymmetric carbon atoms depending on the type of the substituent. Accordingly, any optical isomer in an optically pure form based on the one or more asymmetric carbon atoms, any mixture of optical isomers, racemates, diastereoisomers in pure forms, mixtures of the diastereoisomers, and the like fall within the scope of the present invention. The compounds represented by the general formula (I) may sometimes exist as base addition salts such as sodium salt and potassium salt, or acid addition salts such as hydrochloride, sulfate and p-toluenesulfonate. Any of these salts falls within the scope of the present invention. The compound in a free form or that in a form of a salt may sometimes exist as a hydrate or a solvate, and these substances naturally fall within the scope of the present invention.

Preferred examples of the compounds represented in the general formula (I) will be shown below. However, the scope of the present invention is not limited to the following compounds.

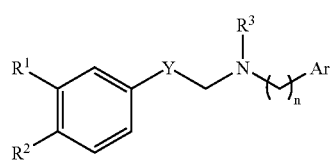

(I)

| Compound No. | $R^1$ | $R^2$ | Y | $R^3$ | n | Ar |
|---|---|---|---|---|---|---|
| SY87 | CH₃O— | CH₃O— | —CH=CH— | H— | 0 | Ph(4-OCH₃) |
| SY88 | H— | HO— | —CH₂— | H— | 1 | Ph(3,4-di-OCH₃) |
| SY90 | H— | HO— | —CH₂— | H— | 1 | Ph(3,4-di-OH) |
| SY94 | H— | CH₃O—CO—CH₂—O— | —CH₂— | CH₃O—CO—CH₂— | 1 | Ph(3,4-di-OCH₃) |
| SY95 | CH₃O— | CH₃O— | —CH=CH— | H— | 1 | Ph(4-F) |
| SY96 | H— | CH₃O— | —CH₂— | CH₃— | 1 | Ph(3,4-di-OCH₃) |
| SY97 | CH₃O— | CH₃O— | —CH=CH— | CH₃O—CO—CH₂— | 1 | Ph(4-F) |
| SY99 | CH₃O— | CH₃O— | —CH=CH— | CH₃— | 1 | Ph(4-F) |
| SY106 | H— | HO— | —CH₂— | H— | 1 | 4-Pyridyl |
| SY107 | H— | HO— | —CH₂— | H— | 1 | 3-Furyl |
| SY109 | H— | HO— | —CH₂— | H— | 1 | Ph(2-OH) |

The compound represented by the aforementioned general formula (I) can easily prepared by, for example, condensing the corresponding amine compound with an aldehyde to synthesize an imine, and reducing the synthesized imine with an appropriate reducing agent. Specific examples will be shown in the examples of the specification. The condensation can be performed without solvent, and also can advantageously be preformed in suitable combination of an appropriate solvent with an acid catalyst. As the reducing agent, sodium borohydride can be used; however, the reducing agent is not limited thereto. The amine generated from the reduction can be modified by, for example, alkylation which is performed by reacting the amine with an appropriate alkyl halide in the presence of a strong base such as sodium hydride. Preparation examples according to the aforementioned preparation method will be specifically shown in the examples of the specification. Therefore, those skilled in the art can prepare any compound represented in the general formula (I) by referring to the aforementioned general descriptions and specific explanations in the examples, and appropriately choosing starting materials, reagents, reaction conditions and the like, and if necessary, by adding suitable modifications and alterations to the aforementioned method.

The compounds represented by the aforementioned general formula (I) or salts thereof have inhibitory action against the abscisic acid biosynthesis, and are useful as, for example, active ingredients of plant growth regulators. In addition, the compounds of the present invention or salts thereof can be used as specific inhibitors against epoxycarotenoid dioxygenase. By applying the compounds of the present invention represented by the aforementioned general formula (I) to plants as plant growth regulators, plant growth, taking root, germination and the like can be promoted. The term "plant growth regulation" used in this specification should be construed in its broadest sense, including, for example, regulation of plant elongation, pollen growth regulation, retention of flower freshness, enhancement of the plant anti-stress property against stresses such as heat, dryness, coldness, diseases and the like, weed control by regulation of reproduction, suppression of plant retrogradation, control of hypertrophy of root. The compounds of the present invention or salts thereof can also be used as, for example, biochemical reagents in the studies for elucidation of the biosynthetic path or the functions of abscisic acid.

The inhibitor against the abscisic acid biosynthesis, the specific inhibitor against epoxycarotenoid dioxygenase, and the plant growth regulator provided by the present invention can be formulated, for example, as an agricultural composition by using formulation additives well known in the art. Forms of the agricultural composition are not particularly limited, and any form that can be used in the art may be chosen. For example, compositions in the forms of emulsions, liquids, oils, water soluble powders, wettable powders, flowables, powders, subtilized granules, granules, aerosols, fumigants, pastes and the like can be used. The methods for manufacturing the agricultural composition are also not particularly limited, and any method available to those skilled in the art can be appropriately employed. As the active ingredient of the inhibitors of the present invention, two or more of the compounds represented by the aforementioned general formula (I) or salts thereof may be used in combination. Further, other active ingredients of agricultural chemicals such as insecticides, fungicides, insecticidal and fungicidal agents, herbicides and the like may be mixed. Methods of application and doses of the inhibitors of the present invention can be suitably chosen by those skilled in the art depending on conditions including a purpose of application, a dosage form, a plot to be treated and the like. The concentration to obtain the optimal action can properly be decided by those skilled in the art by referring to the following examples.

EXAMPLES

The present invention will be explained more specifically with reference to examples. However, the scope of the present invention is not limited to the following examples.

Example 1

Compound SY109
[4-[2-(2-hydroxy-benzylamino)-ethyl]-phenol]

(a) Synthesis of Compound SY108 [4-{2-[(2-hydroxy-benzylidene)-amino]-ethyl}-phenol]

4-Hydroxyphenethylamine (1.37 g, 10 mmol) and 2-hydroxybenzylamine (1.22 g, 10 mmol) were reacted with heating under reflux in toluene. After the reaction was terminated, the solvent was evaporated under reduced pressure, and purification was performed by silica gel column chromatography (hexane/ethyl acetate) to obtain the desired imine. Yield 2.15 g.

$^1$H-NMR (MeOH-$d_6$) δ 7.25 (1H, s), 7.36-7.23 (2H, m), 7.06 (2H, d), 6.85 (2H, m), 6.72 (2H, d), 4.90 (2H, br s), 3.82 (2H, t), 2.92 (2H, t)

(b) Synthesis of Compound SY109

Compound SY108 (1.2 g, 5 mmol) was dissolved in ethanol (20 ml), and added with an excess amount of sodium borohydride with stirring. The progress of the reaction was monitored by using thin layer chromatography. After the starting material disappeared, the reaction was terminated, and water (50 ml) was added to the reaction mixture. The ethanol was evaporated under reduced pressure, and the aqueous layer was extracted three times with ethyl acetate, and then the extract was dried, concentrated, and purified by using silica gel column chromatography (chloroform/ethyl acetate) to obtain the desired compound. Yield 0.8 g.

$^1$H-NMR (CDCl$_3$+Acetone-$d_6$) δ 7.08 (1H, t), 6.97 (2H, d), 6.91 (2H, d), 6.74 (2H, d), 6.76-6.67 (2H, m), 3.91 (2H, s), 2.87 (2H, t), 2.72 (2H, t)

Example 2

Compound SY94 [{(3,4-dimethoxy-benzyl)-[2-(4-methoxycarbonylmethoxy-phenyl)-ethyl]-amino}-acetic acid methyl ester]

(a) Compound SY73 [4-{2-[(3,4-dimethoxy-benzylidene)-amino]-ethyl}-phenol]

Compound SY73 was obtained in the same manner as in Example 1(a).

$^1$H-NMR (Acetone-$d_6$) δ 8.14 (1H, s), 7.46 (1H, s), 7.19 (1H, d), 7.09 (2H, d), 6.99 (1H, d), 6.77 (2H, d), 3.86 (3H, s), 3.85 (3H, s), 3.74 (2H, t), 2.87 (2H, t)

(b) Synthesis of Compound SY88
[4-[2-(3,4-dimethoxy-benzylamino)-ethyl]-phenol]

Compound SY88 was obtained in the same manner as in Example 1(b).

$^1$H-NMR (CDCl$_3$+Acetone-$d_6$) δ 6.98 (2H, d), 6.73 (1H, s), 6.67-6.63 (4H, m), 3.73 (3H, s), 3.72 (3H, s), 3.61 (2H, s), 2.75-2.70 (2H, m), 2.64-2.60 (2H, m)

(c) Synthesis of Compound SY94

Compound SY88 (287 mg, 1 mmol) was dissolved in dry dimethylformamide (3 ml), and the solution was added with 1.3 equivalents of sodium hydride and stirred for 10 minutes. Then, 1.3 equivalents of brominated methyl acetate were added, and the reaction was carried out at room temperature for 4 hours. After the reaction was terminated, the reaction mixture was poured into water (20 ml) and extracted three times with ethyl acetate. The extract was dried, concentrated, and purified by silica gel column chromatography to obtain the desired compound. Yield 125 mg.

$^1$H-NMR (CDCl$_3$) δ 7.08 (2H, d), 6.87 (1H, s), 6.78 (2H, d), 6.76 (2H, m), 4.59 (2H, s), 3.85 (3H, s), 3.83 (3H, s), 3.78 (3H, s), 3.75 (2H, s), 3.67 (3H, s), 3.35 (2H, s), 2.80-2.85 (2H, m), 2.76-2.71 (2H, m)

Example 3

The following intermediate compounds and the compounds of the present invention were prepared in the same manner as in Examples 1 and 2.

Compound SY72 [4-{[2-(4-hydroxy-phenyl)-ethylimino]-methyl}-benzene-1,2-diol $^1$H-NMR (Acetone-d$_6$+DMSO-d$_6$) δ 8.03 (1H, s), 7.31 (1H, s), 7.06 (2H, d), 6.90 (1H, d), 6.80 (1H, d), 6.72 (2H, d), 3.68 (2H, t), 3.15 (3H, br s), 2.82 (2H, t)

Compound SY76
[3-(3,4-dimethoxy-phenyl)-prop-2-ene-1-ol]

$^1$H-NMR (Acetone-d$_6$) δ 7.08 (1H, s), 7.07-6.87 (2H, m), 6.54 (1H, d), 6.29 (1H, td), 4.23 (2H, d), 3.84 (3H, s), 3.80 (3H, s), 3.05(1H, br s)

Compound SY78
[3-(3,4-dimethoxy-phenyl)-propenal]

$^1$H-NMR (CDCl$_3$) δ 7.44 (1H, d), 7.17 (1H, d), 7.09 (1H, s), 6.93 (1H, d), 6.63 (1H, dd), 3.96 (3H, s), 3.95 (3H, s), 9.68 (1H, d)

Compound SY83 [[3-(3,4-dimethoxy-phenyl)-allylidene]-(4-methoxy-phenyl)-amine]

$^1$H-NMR (Acetone-d$_6$) δ 8.37 (1H, s), 7.33 (1H, s), 7.32-7.15 (4H, m), 7.05-6.94 (4H, m), 3.93 (3H, s), 3.87 (3H, s), 3.83 (3H, s)

Compound SY93 [[3-(3,4-dimethoxy-phenyl)-allylidene]-(4-fluoro-benzyl)-amine]

$^1$H-NMR (Acetone-d$_6$) δ 8.19 (1H, d), 7.42-7.26 (3H, m), 7.15-6.83 (6H, m), 4.67 (2H, s), 3.89 (3H, s), 3.85 (3H, m)

Compound SY104 [4-{2-[(pyridin-4-ylmethylene)-amino]-ethyl}-phenol]

$^1$H-NMR (Acetone-d$_6$) δ 8.68 (2H, d), 8.26 (1H, s), 7.67 (2H, d), 7.09 (2H, d), 6.76 (2H, d), 3.86 (2H, t), 2.94 (1H, br s), 2.91 (2H, t)

Compound SY105 [4-{2-[(furan-3-ylmethylene)-amino]-ethyl}-phenol]

$^1$H-NMR (Acetone-d$_6$) δ 8.19 (1H, s), 7.91 (1H, s), 7.59 (1H, s), 7.06 (2H, d), 6.81 (1H, s), 6.75 (2H, d), 3.71 (2H, t), 2.89 (1H, br s), 2.843 (2H, t)

Compound SY87 [[3-(3,4-dimethoxy-phenyl)-allyl]-(4-methoxy-phenyl)-amine]

$^1$H-NMR (MeOH-d$_6$) δ 7.44 (2H, d), 7.14-6.94 (5H, m), 6.78 (1H, d), 6.19 (1H, td), 4.89 (1H, br s), 4.14 (2H, d), 3.87 (9H, s)

Compound SY90 [4-{[2-(4-hydroxy-phenyl)-ethylamino]-methyl}-benzene-1,2-diol]

$^1$H-NMR (MeOH-d$_6$) δ 7.09 (2H, d), 7.01 (1H, s), 6.87 (2H, m), 6.79 (2H, d), 4.95 (4H, br s), 4.06 (2H, s), 3.17 (2H, m), 2.81 (2H, m)

Compound SY95 [[3-(3,4-dimethoxy-phenyl)-allyl]-(4-fluoro-benzyl)-amine]

$^1$H-NMR (MeOH-d$_6$) δ 7.58 (2H, m), 7.27-7.05 (4H, m), 6.97 (1H, d), 6.84 (1H, d), 6.20 (1H, td), 4.89 (1H, br s), 4.26 (2H, s), 3.88 (3H, s), 3.87 (3H, s), 3.84 (2H, d)

Compound SY96 [(3,4-dimethoxy-benzyl)-[2-(4-methoxy-phenyl)-ethyl]-methyl-amine]

$^1$H-NMR (CDCl$_3$) δ 7.12 (2H, d), 7.86 (2H, d), 6.86 (3H, m), 3.89 (3H, s), 3.87 (3H, m), 3.80 (3H, s), 3.51 (2H, s), 2.82-2.77 (2H, m), 2.65-2.60 (2H, m), 2.30 (3H, s)

Compound SY97 [[[3-(3,4-dimethoxy-phenyl)-allyl]-(4-fluoro-benzyl)-amino]-acetic acid methyl ester]

$^1$H-NMR (CDCl$_3$) δ 7.34 (2H, m), 7.03-6.87 (4H, m), 6.79 (1H, d), 6.47 (1H, d), 6.22-6.12 (1H, td), 3.89 (3H, s), 3.86 (3H, s), 3.77 (2H, s), 3.66 (3H, s), 3.38 (2H, d), 3.34 (2H, s)

Compound SY99 [[3-(3,4-dimethoxy-phenyl)-allyl]-(4-fluoro-benzyl)-methyl-amine]

$^1$H-NMR (CDCl$_3$) δ 7.31 (2H, m), 7.05-6.97 (4H, m), 6.82 (1H, d), 6.48 (1H, d), 6.22-6.12 (1H, td), 3.90 (3H, s), 3.88 (3H, s), 3.52 (2H, s), 3.17 (2H, d), 2.23 (3H, s)

Compound SY106 [4-{2-[(pyridin-4-ylmethyl)-2-amino]-ethyl}-phenol]

$^1$H-NMR (Acetone-d$_6$) δ 8.47 (2H, d), 7.33 (2H, d), 7.05 (2H, d), 6.75 (2H, d), 3.83 (2H, s), 2.88 (2H, br s), 2.82-2.77 (2H, m), 2.74-2.69 (2H, m)

Compound SY107 [4-{2-[(furan-3-ylmethyl)-amino]-ethyl}-phenol]

$^1$H-NMR (Acetone-d$_6$) δ 7.45 (2H, d), 7.05 (2H, d), 6.75 (2H, d), 6.42(1H, s), 3.63 (2H, s), 2.90 (2H, br s), 2.81-2.76 (2H, m), 2.72-2.61 (2H, m)

Test Example 1

The inhibitory action against epoxycarotenoid dioxygenase was studied. The test was carried out according to the method described in The Plant Journal (2001) 27(4), 325-333. As a result, it was demonstrated that NDGA [4,4'-(2,3-dimethyl-1,4-butanediyl)bis-1,2-benzenediol] completely inhibited the cleavage reaction of neoxanthin by NCED at the concentration of 100 µM. Accordingly, it was concluded that this compound exhibits inhibitory activity against the abscisic acid biosynthesis by inhibiting NCED.

Test Example 2

Inhibitory tests against pore closing were carried out by using the aforementioned compounds. In these tests, plants in the state that their pores are open are treated with the compounds, and closings of the pores are examined when the plants are transferred into a mannose solution of high concentration to make the pores closed. Pore closing is caused by the effect of abscisic acid biosynthesized in the body of a plant that has detected the change of the mannose concentration. The test was carried out according to the method described in the literature of Plant Physiology (1992) 99, 1258-1260 and by using spinach as a material.

As a result, Compounds SY109, 87, 94, 99, 96, 97, and 95 were found to have potent inhibitory activities against pore closing. When the plants treated with these compounds were added with abscisic acid, pores of the plants closed, whereas when the plants treated with NDGA were added with abscisic acid, pores of the plant did not close. These results are considered to be derived from an undesired influence of NDGA on some actions of plants other than the abscisic acid biosynthesis to exert the toxicity. From these results, it was concluded that the compounds of the present invention are more specific inhibitors against the abscisic acid biosynthesis than NDGA.

Test Example 3

The NCED inhibitory activity of the compounds of the present invention was studied. As a result, each of the compounds, SY109, 87, 94, 99, 96, 97, and 95, was found to have 30 to 100% NCED inhibitory activity at the concentration of 100 µM.

Test Example 4

The compounds of the present invention were applied to plant bodies. Hypocotyls of Mung bean on the 6th-day after seeding, that were grown at 25° C., were cut in water with razor, and the hypocotyl parts were soaked by 2 cm in solutions of the compounds at a given concentration. On the 6th day after the soaking, the lengths of the roots were measured. The following results were shown as an average length per root.

TABLE 2

| Compound | Length (cm) |
| --- | --- |
| SY87 | 0.6 |
| SY88 | >0.1 |
| SY90 | >0.1 |
| SY94 | 2.1 |
| SY95 | 0.6 |
| SY96 | 1.5 |
| SY97 | 0.7 |

TABLE 2-continued

| Compound | Length (cm) |
| --- | --- |
| SY99 | 0.4 |
| SY106 | >0.1 |
| SY107 | >0.1 |
| SY109 | 1.5 |
| Control | >0.1 |

Test Example 5

The germination rate of seeds of barley, which had significantly lowered germination rate, was compared between the seeds after treatment with the compounds and the seeds without the treatment. In the test, 2 sheets of filter paper were placed in a 15 cm laboratory dish, and each of the test solutions of the compounds at a given concentration (10 ml) was added to the dish, and 100 seeds were put on the paper and cultured under a light at 25° C. Ratios of germinated seeds were calculated after one week.

TABLE 3

| Compound | Germination rate (%) |
| --- | --- |
| SY87 | 40 |
| SY88 | 8 |
| SY90 | 12 |
| SY94 | 52 |
| SY95 | 29 |
| SY96 | 21 |
| SY97 | 18 |
| SY99 | 15 |
| SY106 | 9 |
| SY107 | 10 |
| SY109 | 35 |
| Control | 9 |

INDUSTRIAL APPLICABILITY

The compounds of the present invention have inhibitory action against the abscisic acid biosynthesis, and are useful as plant growth regulators for promoting plant growth, taking root, germination and the like.

What is claimed:

1. A method for regulating plant growth comprising applying to a plant, a compound represented by the following general formula (I) or a salt thereof:

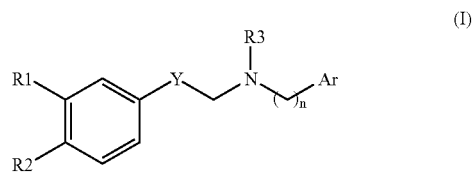

wherein $R^1$ represents hydrogen atom, hydroxyl group, or alkoxy group; $R^2$ represents hydroxyl group or an alkoxy group which may be substituted; $R^3$ represents hydrogen atom or an alkyl group which may be substituted; Y represents —CH=CH— or —CH$_2$—; n represents 0 or 1; Ar represents an aryl group which may be substituted.

2. A method of claim 1, wherein the method inhibits abscisic acid biosynthesis in a plant body.

3. A method of claim 1, wherein the method inhibits epoxy-carotenoid dioxygenase in a plant body.

4. A method of claim 1, wherein $R^1$ is methoxy.

5. A method of claim 1, wherein $R^2$ is methoxy.

6. A method of claim 4, wherein $R^2$ is methoxy.

7. A method of claim 2, wherein $R^1$ is methoxy.

8. A method of claim 2, wherein $R^2$ is methoxy.

9. A method of claim 7, wherein $R^2$ is methoxy.

10. A method of claim 3, wherein $R^1$ is methoxy.

11. A method of claim 3, wherein $R^2$ is by methoxy.

12. A method of claim 10, wherein $R^2$ is by methoxy.

* * * * *

UNITED STATES PATENT AND TRADEMARK OFFICE
CERTIFICATE OF CORRECTION

PATENT NO. : 7,432,228 B2
APPLICATION NO. : 11/362415
DATED : October 7, 2008
INVENTOR(S) : S. Yoshida et al.

Page 1 of 1

It is certified that error appears in the above-identified patent and that said Letters Patent is hereby corrected as shown below:

On the title page, at Item (56), References Cited, Other Publications, "Di Plama" should be --Di Palma--.

Signed and Sealed this

Fifth Day of May, 2009

JOHN DOLL
*Acting Director of the United States Patent and Trademark Office*